US008071287B2

(12) United States Patent
Liggett

(10) Patent No.: US 8,071,287 B2
(45) Date of Patent: Dec. 6, 2011

(54) PHARMACEUTICAL AND THERAPEUTIC APPLICATIONS RELATING TO A TYPE 9 ADENYLYL CYCLASE POLYMORPHISM IN ASTHMA AND REVERSIBLE BRONCHIAL OBSTRUCTION

(76) Inventor: Stephen B. Liggett, Clarksville, MD (US)

( * ) Notice: Subject to any disclaimer, the term of this patent is extended or adjusted under 35 U.S.C. 154(b) by 308 days.

(21) Appl. No.: 11/912,205

(22) PCT Filed: Apr. 24, 2006

(86) PCT No.: PCT/US2006/015221
§ 371 (c)(1),
(2), (4) Date: Sep. 3, 2008

(87) PCT Pub. No.: WO2006/116174
PCT Pub. Date: Nov. 2, 2006

(65) Prior Publication Data
US 2009/0149376 A1 Jun. 11, 2009

Related U.S. Application Data

(60) Provisional application No. 60/673,924, filed on Apr. 22, 2005.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 5,541,308 A | 7/1996 | Hogan et al. |
| 2001/0041718 A1 | 11/2001 | Thompson et al. |
| 2002/0142436 A1 | 10/2002 | Antoni et al. |

OTHER PUBLICATIONS

Nelson et al, "Advair: Combination treatment with fluticasone propionate/salmeterol in the treatment of asthma," J. Allergy Clin. Immunol., vol. 107, No. 2, pp. 398-416. Feb. 2000.

Small et al, "An Ile Met polymorphism in the catalytic domain of adenylyl cyclase type 9 confers reduced Beta-2-adrenergic receptor stimulation," Pharmacogenetics 2003, vol. 13, No. 9, pp. 535-541.
Drysdale et al, "Complex promoter and coding region Beta-2-adrenergic receptor haplotypes alter receptor expression and predict in vivo responsiveness," PNAS, Sep. 12, 2000, vol. 97, No. 19, pp. 10483-10488.
Aksoy et al., "Glucocorticoid effects on the β-adrenergic receptor-adenylyl cyclase system of human airway epithelium," J. Allergy Clin. Immunol., Mar. 2002, vol. 109, No. 3, pp. 492-497.
Drazen et al., "Heterogeneity of therapeutic responses in asthma," British Medical Bulletin, 2000, vol. 56, No. 4, pp. 1054-1070.
Israel et al., "Use of regularly scheduled albuterol treatment in asthma: genotype-stratified, randomised, placebo-controlled crossover trial," www.thelancet.com., Oct. 23, 2004, vol. 364, pp. 1505-1512.
Lima et al., "Impact of genetic polymorphisms of the β2-adrenergic receptor on albuterol bronchodilator pharmacodynamics," Clinical Pharmacology & Therapeutics, May 1999, vol. 65, No. 5, pp. 519-525.
Mialet-Perez et al., "A primate-dominant third glycosylation site of the β2-adrenergic receptor routes receptors to degradation during agonist regulation," The Journal of Biological Chemistry, Sep. 10, 2004, vol. 279, No. 37, pp. 38603-38607.
Silverman et al., "Family-based association analysis of β2-adrenergic receptor polymorphisms in the childhood asthma management program," J. Allergy Clin. Immunol., Nov. 2003, vol. 112, No. 5, pp. 870-876.
Drysdale C.M., et al., Proceedings the National Academy of Sciences, USA, Sep. 12, 2000, vol. 97, No. 19, pp. 10483-10488.
"Long-Term Effects of Budesonide or Nedocromil in Children With Asthma," The New England Journal of Medicine, vol. 343, Oct. 12, 2000, No. 15.
"B1-adrenergic receptor polymorphisms confer differential function and predisposition to heart failure," Perez, J.M., et al., Nature Medicine, vol. 9, No. 10, Oct. 2003, pp. 1300-1305.
Genetics of Asthma, Marcel Dekker, Inc., New York, pp. 91-117 (1996).

*Primary Examiner* — Michael Pak
(74) *Attorney, Agent, or Firm* — Dinsmore & Shohl LLP

(57) ABSTRACT

A pharmaceutical composition comprising an expression product of a Type Nine adenylyl cyclase gene polymorphism, along with a suitable physiological carrier, are provided. In addition, methods related to treating patients having asthma or a reversible bronchial obstruction, kits for determining the responsiveness of an individual to treatment regimens, and assays for screening pharmaceutical for efficacy in treatment are also provided.

2 Claims, 6 Drawing Sheets

MASPPHQQLLHHHSTEVSCDSSGDSNSVRVKINPKQLSSNSHPKHCKYSISSSCSSSGDSGG
VPRRVGGGGRLRRQ
KKLPQILFERASSRWWDPKFDSVNLEEACLERCFPQTQRRFRYALFYIGFACLLWSIYFAVH
MRSRLIVMVAPALCF
LLVCVGFFLFTFTKLYARHYAWTSLALTLLVFALTLAAQFQVLTPVSGRGDSSNLTATARP
TDTCLSQVGSFSMCI
EVLFLLYTVMHLPLYLSLCLGVAYSVLFETFGYHFRDEACFPSPGAGALHWELLSRGLLH
GCIHAIGVHLFVMSQV
RSRSTFLKVGQSIMHGKDLEVEKALKERMIHSVMPRIIADDLMKQGDEESENSVKRHATSS
PKNRKKKSSIQKAPI
AFRPFKMQQIEEVSILFADIVGFTKMSANKSAHALVGLLNDLFGRFDRLCEETKCEKISTLG
DCYYCVAGCPEPRA
DHAYCCIEMGLGMIKAIEQFCQEKKEMVNMRVGVHTGTVLCGILGMRRFKFDVWSNDV
NLANLMEQLGVAGKVHIS
EATAKYLDDRYEMEDGKVIERLGQSVVADQLKGLKTYLISGQRAKESRCSCAEALLSGFE
VIDGSQVSSGPRGQGT
ASSGNVSDLAQTVKTFDNLKTCPSCGITFAPKSEAGAEGGAPQNGCQDEHKNSTKASGGP
NPKTQNGLLSPPQEEK
LTNSQTSLCEILQEKGRWAGVSLDQSALLPLRFKNIREKTDAHFVDVIKEDSLMKDYFFKP
PINQFSLNFLDQELE
RSYRTSYQEEVMKNSPVKTFASPTFSSLLDVFLSTTVFLTLSTTCFLKYEAATVPPPPAALA
VFSAALLLEVLSLA
VSIRMVFFLEDVMACTKRLLEWIAGWLPRHCIGAILVSLPALAVYSHVTSEYETNIHFPVFT
GSAALIAVVHYCNF
CQLSSWMRSSLATVVGAGPLLLLYVSLCPDSSVLTSPLDAVQNFSSERNPCNSSVPRDLRR
PASLIGQEVVLVFFL
LLLLVWFLNREFEVSYRLHYHGDVEADLHRTKIQSMRDQADWLLRNIIPYHVAEQLKVSQ
TYSKNHDSGGVIFASI
VNFSEFYEENYEGGKECYRVLNELIGDFDELLSKPDYSSIEKIKTIGATYMAASGLNTAQA
QDGSHPQEHLQILFE
FAKEMMRVVDDFNNNMLWFNFKLRVGFNHGPLTAGVIGTTKLLYDIWGDTVNIASRMD
TTGVECRIQVSEESYRVL
SKMGYDFDYRGTVNVKGKGQMKTYLYPKCTDHRVIPQHQLSISPDIRVQVDGSIGRSPTD
EIANLVPSVQYVDKTS
LGSDSSTQAKDAHLSPKRPWKEPVKAEERGRFGKAIEKDDCDETGIEEANELTKLNVSKSV
*

Figure 5

```
ATGGCTTCCCCGCCCCACCAGCAGCTGCTGCATCACCACAGGACCGAGGTGAGCTGCGACTCCAGCGGGGACAGCA
ACAGCGTGCGCGTCAAGATCAACCCCAAGCAGCTGTCCTCCAACAGCCACCCCAAGCACTGCAAATACAGCATCTC
CTCTAGCTGCAGCAGCTCTGGGGACTCCGGGGGCGTCCCCCGGCGAGTGGGCGGCGGAGGCCGGCTGCGCAGGCAG
AAGAAGCTGCCCCAGCTGTTCGAGAGGGCCTCCAGCCGCTGGTGGGACCCCAAGTTCGACTCGGTGAACCTGGAGG
AGGCCTGCCTGGAGCGCTGCTTCCCGCAGACCCAGCGCCGGTTCCGGTATGCGCTCTTCTACATCGGCTTCGCCTG
CCTTCTGTGGAGCATCTATTTTGCGGTCCACATGAGATCCAGACTGATCGTCATGGTCGCCCCCGCGCTGTGCTTC
CTCCTGGTGTGTGTGGGCTTCTTTCTGTTTACCTTCACCAAGCTGTACGCCCGGCATTACGCGTGGACCTCGCTGG
CTCTCACCCTGCTGGTGTTCGCCCTGACCCTGGCTGCGCAGTTCCAGGTCTTGACGCCTGTCTCAGGACGCGGCGA
CAGCTCCAACCTTACGGCCACAGCCCGGCCCACAGATACTTGCTTATCTCAAGTGGGGAGCTTCTCCATGTGCATC
GAAGTGCTCTTTTTGCTCTATACCGTCATGCACTTACCTTTGTACCTGAGTTTGTGTCTGGGGGTGGCCTACTCTG
TCCTTTTCGAGACCTTTGGCTACCATTTCCGGGATGAAGCCTGCTTCCCCTCGCCCGGAGCCGGGGCCCTGCACTG
GGAGCTGCTGAGCAGGGGGCTGCTCCACGGCTGCATCCACGCCATCGGGGTCCACCTGTTCGTCATGTCCCAGGTG
AGGTCCAGGAGCACCTTCCTCAAGGTGGGGCAATCCATTATGCACGGGAAGGACCTGGAAGTGGAAAAAGCCCTCA
AAGAGAGGATGATTCATTCCGTGATGCCAAGAATCATAGCCGATGACTTAATGAAGCAGGGAGATGAGGAGAGTGA
GAATTCTGTCAAGAGGCATGCCACCTCGAGCCCCAAGAACAGGAAGAAAAAGTCTTCCATCCAAAAAGCTCCTATA
GCCTTCCGCCCTTTTAAGATGCAGCAGATCGAAGAAGTCAGTATCTTATTTGCAGATATCGTGGGCTTCACCAAGA
TGAGTGCCAACAAGTCTGCCCACGCCCTGGTGGGTCTCCTGAACGATCTGTTCGGTCGCTTCGACCGCCTGTGTGA
GGAGACCAAGTGTGAGAAAATCAGCACCCTGGGAGACTGTTACTACTGCGTGGCGGGCTGTCCCGAGCCCCGGGCC
GACCATGCCTACTGCTGCATCGAGATGGGCCTGGGCATGATCAAGGCCATCGAGCAGTTCTGCCAGGAGAAGAAGG
AGATGGTGAACATGAGAGTCGGGGTGCACACGGGCACCGTCCTTTGCGGCATCCTGGGCATGAGGAGGTTTAAATT
TGACGTGTGGTCCAACGATGTGAACCTGGCCAATCTCATGGAGCAGCTGGGAGTGGCCGGCAAAGTTCACATTTCT
GAGGCCACCGCAAAATACTTAGATGACCGGTACGAAATGGAAGATGGGAAAGTTATTGAACGGCTGGGCCAGAGCG
TGGTTGCTGACCAGTTGAAAGGTTTGAAGACATACCTGATATCGGGTCAGAGAGCCAAGGAGTCTCGCTGCAGCTG
TGCAGAGGCCTTGCTTTCTGGCTTTGAGGTCATTGACGGCTCACAGGTGTCCTCAGGCCCTAGGGGACAGGGGACA
GCGTCATCAGGGAATGTCAGTGACTTGGCGCAGACTGTCAAAACCTTTGATAACCTTAAGACCTGCCCTTCGTGCG
GAATCACATTTGCTCCCAAATCTGAAGCCGGCGCCGAGGGAGGAGCACCTCAAAACGGCTGCCAAGACGAGCATAA
AAACAGCACCAAGGCTTCTGGAGGACCTAATCCCAAAACTCAGAACGGGCTCCTCAGCCCTCCCCAAGAGGAGAAG
CTCACCAACAGTCAGACTTCTCTGTGTGAGATCTTGCAGGAGAAGGGAAGGTGGGCAGGGGTGAGCCTGGACCAGT
CGGCTCTCCTTCCGCTGAGGTTCAAGAACATCCGGGAGAAAACGGACGCCCACTTTGTGGACGTTATCAAAGAAGA
CAGCCTGATGAAAGATTACTTTTTTAAGCCGCCCATTAATCAGTTCAGCCTGAACTTCCTGGATCAGGAGCTGGAG
CGATCCTACAGGACCAGCTATCAGGAAGGAGGTACAGAAGAACTCCCCCGTGAAGACGTTTGCTAGTCCCACCTTCA
GCTCCCTCCTGGATGTGTTTCTGTCGACCACAGTGTTTCTGACGCTGTCCACCACCTGCTTCCTGAAGTACGAGGC
GGCCACCGTGCCTCCCCGCCCGCCGCCCTGGCGGTCTTCAGTGCAGCCCTGCTGCTGGAGGTGCTGTCCCTCGCG
GTGTCCATCAGGATGGTGTTCTTCCTGGAGGACGTCATGGCCTGCACCAAGCGCCTGCTGGAGTGGATCGCCGGCT
GGCTACCACGTCACTGCATCGGGGCCATCCTGGTGTCGCTTCCCGCACTGGCCGTCTACTCCCATGTCACCTCCGA
ATATGAGACCAACATACACTTCCCAGTGTTCACAGGCTCGGCCGCGCTGATTGCCGTCGTGCACTACTGTAACTTC
TGCCAGCTCAGCTCCTGGATGAGGTCCTCCCTCGCCACCGTCGTGGGGGCCGGGCCGCTGCTCCTGCTCTACGTCT
CCCTGTGCCCAGACAGTTCTGTATTAACTTCGCCCCTTGACGCAGTACAGAATTTCAGTTCCGAGAGGAACCCGTG
CAATAGTTCGGTGCCGCGTGACCTCCGGCGGCCCGCCAGCCTCATCGGCCAGGAGGTGGTTCTCGTCTTCTTTCTC
CTGCTCTTGTTGGTCTGGTTCCTGAATCGCGAATTTGAAGTCAGCTACCGCCTCCACTACCACGGAGACGTGGAAG
CGGATCTTCACCGCACCAAGATCCAGAGCATGCGGGACCAGGCAGACTGGCTGCTGAGGAACATCATCCCCTACCA
CGTGGCTGAGCAGCTGAAGGTGTCCCAGACCTACTCCAAGAACATGACAGCGGAGGGGTGATCTTCGCCAGCATC
GTCAACTTCAGCGAGTTCTACGAGGAGAACTACGAGGGCGGCAAGGAGTGCTACCGGGTCCTCAACGAGCTCATCG
GGGACTTTGACGAGCTCCTAAGCAAGCCGGACTACAGCAGCATCGAGAAGATCAAGACCATCGGACGCCACGTACAT
GGCGGCGTCAGGGCTGAACACCGCGCAGGCCCAGGACGGCAGCCACCCGCAGGAGCACCTGCAGATCCTGTTCGAG
TTCGCCAAGGAGATGATGCGCGTGGTGGACGACTTCAACAACAACATGCTGTGGTTCAACTTCAAGCTCCGCGTCG
GCTTCAACCATGGGCCCCTCACGGCCGGGGTCATCGGCACCACCAAGCTGCTGTACGACATCTGGGGAGACACCGT
CAACATCGCCAGCAGGATGGACACCACCGGCGTGGAGTGCCGCATCCAGGTGAGCGAAGAGAGCTACCGCGTCTTG
AGCAAGATGGGCTATGACTTCGACTACAGAGGGACCGTGAATGTCAAGGGGAAAGGCCAGATGAAGACCTACCTGT
ACCCAAAGTGCACGGATCACAGGGTCATCCCACAGCAGTCGTCCATCTCCCCAGACATCCGCGTCCAGGTGGA
TGGCAGCATCGGACGGTCTCCCACAGACGAGATTGCCAACCTGGTGCCTTCTGTCCAGTATGTGGACAAGACATCT
CTGGGTTCTGACAGCAGCACGCAGGCCAAGGATGCCCACCTGTCCCCCAAGAGACCGTGGAAGGAGCCCGTCAAAG
CCGAAGAAAGGGGTCGATTTGGCAAAGCCATAGAGAAAGACGACTGTGACGAAACAGGAATAGAAGAAGCCAACGA
ACTCACCAAGCTCAACGTTTCAAAGAGTGTGTGA
```

PHARMACEUTICAL AND THERAPEUTIC APPLICATIONS RELATING TO A TYPE 9 ADENYLYL CYCLASE POLYMORPHISM IN ASTHMA AND REVERSIBLE BRONCHIAL OBSTRUCTION

RELATED APPLICATION

The present application claims priority to U.S. provisional patent application Ser. No. 60/673,924, filed on Apr. 22, 2005.

TECHNICAL FIELD

The present invention relates to pharmaceutical compositions and methods for treating asthma and other reversible bronchial obstructions. Specifically, the invention provides novel pharmaceutical compositions, pharmaceutical agent screening assays, and predicative and therapeutic methods based on the surprising discovery of an interaction between the presence of a type 9 adenylyl cyclase polymorphism and the efficacy of certain bronchodilators in conjunction with corticosteroid co-administration in affected patients.

BACKGROUND

Asthma is a chronic inflammatory disease of the airways characterized by contraction of airway smooth muscle due to actions of multiple local bronchoconstrictive substances. The syndrome affects ~300 million individuals worldwide and is a substantial international health care burden. The inflammatory component of asthma is typically treated with corticosteroids, while the bronchoconstriction is treated with β-agonist bronchodilators, which as a class are the most prescribed therapeutic regimen for asthma treatment worldwide. Hence, the most commonly employed pharmacological treatment regimen indicated for asthma is co-administration of a bronchodilator and a corticosteroid. Significantly, however, corticosteroids are usually not indicated for intermittent asthma.

Problematically, the clinical response to β-agonists in the treatment of asthma displays a high degree of inter-individual variation that is not readily reconciled by clinical characteristics or baseline lung function. A significant fraction of patients appear to obtain no objective or subjective improvement with β-agonists, particularly when administered on a regularly scheduled regimen. Indeed, a recent analysis has estimated that ~60% of the population variance in the forced expiratory volume in one second ($FEV_1$) response to albuterol (a relatively selective Beta$_2$-adrenergic bronchodilator and the active ingredient in PROVENTIL HFA) can be attributed to genetic variation. See Drazen, J. M., Silverman, E. K. and Lee, T. H. (2000) "Heterogeneity of therapeutic responses in asthma," Br. Med. Bull., 56, 1054-1070.

Therefore, further delineating the genetic basis of β-agonist responsiveness based on the role of other key genes in the early portion of the signal transduction pathway provides a potential basis for understanding the inter-individual variation, and provides additional targets for pharmacological intervention. In view of the marked heterogeneity in response to the most common treatment regimen for asthma, and given that some forms of asthma, and certain other reversible bronchial obstruction disorders which operate at least partly through the same mechanisms, can be symptomatically acute and life-threatening, there is an urgent need in the art for rapid methods of determining whether a given patient will be responsive to certain treatment regimens. In addition there is a need for methods of screening populations of asthmatic and other reversible bronchial obstruction patients in order to identify individuals who will not benefit from treatment regimens that expose the patient to a risk of serious side effects. Further, there is a need to develop treatment regimens which account for the clinically observed inter-individual variation in $β_2AR$ agonist response and a need for the development of screening assays for pharmaceutical agents with bronchodilation efficacy in the population of asthma and/or reversible bronchial obstruction patients which do not respond optimally to conventional treatment.

SUMMARY OF THE INVENTION

Accordingly, the present inventor focused on the effector component protein in the $β_2AR$ signaling pathway, adenylyl cyclase. In particular, the in vitro and in vivo phenotypes of a nonsynonymous polymorphism of adenylyl cyclase type 9 (AC9) were examined. This polymorphism was previously identified and comprises one nonsynonymous single nucleotide polymorphism (SNP), which results in a substitution of Ile for Met at amino acid 772. In contraindication to results of previous studies which suggest the opposite, the present inventor surprisingly discovered that presence of the Met772 polymorphism of AC9 imparts enhanced $β_2AR$ signal transduction in a corticosteroid-specific manner, and, in human asthma, the polymorphism is associated with enhanced β-agonist bronchodilator response under circumstances when corticosteroids are co-administered.

Hence, the present invention provides embodiments directed to pharmaceutical compositions, methods of treating patients having asthma or a reversible bronchial obstruction, methods for identifying a patient who is a candidate for an effective treatment based on the presence of the AC9-Met722 allelic variant, kits for rapid clinical determination of whether an individual will be responsive to a treatment with a pharmaceutical agent, assays for screening pharmaceutical agents for efficacy in the treatment of asthma or reversible bronchial obstruction, methods for predicting the response to treatment with a $β_2AR$ agonist in a patient having asthma or a reversible bronchial obstruction wherein the patient is taking at least one corticosteroid, and methods for determining whether a patient having asthma or a reversible bronchial obstruction will be responsive to a particular treatment regimen.

BRIEF DESCRIPTION OF THE FIGURES

FIG. 5. Amino acid sequence comprising AC9-Met722 polymorphism

FIG. 6. DNA sequence comprising AC9-Met722 gene polymorphism

DETAILED DESCRIPTION

Figure 1:
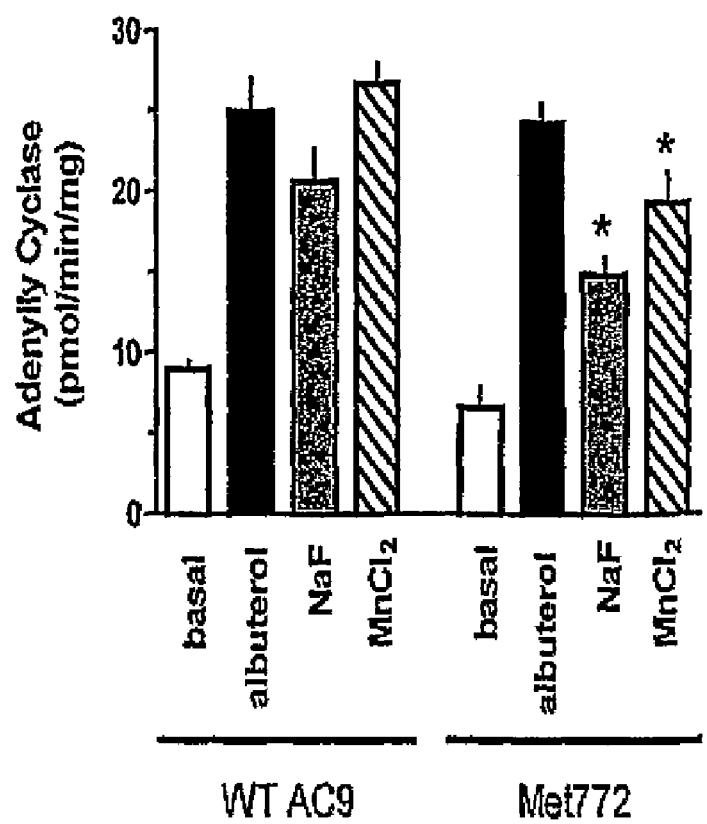
FIG. 1. Characteristics of WT and Met772 AC9 in transfected A431 cells. Shown are the results from adenylyl cyclase studies performed in membranes from cells expressing the same levels of transfected WT and Met772 AC9. $MnCl_2$ and NaF stimulated activities were lower in Met772 cells compared to WT. Results are from 5 experiments. *, P<0.05 compared to WT.

The following abbreviations are used throughout the present disclosure: AC9, adenylyl cyclase type 9; $β_2AR$, $β_2$-adrenergic receptor; 7-TM, seven transmembrane; $G_s$, stimulatory guanine nucleotide binding protein; $FEV_1$, forced expiratory volume in 1 sec; FVC, forced vital capacity; $^{125}$I-CYP, $^{125}$I-cyanopindolol; WT, wild-type (Ile772) allele.

The subject matter of all references cited in this disclosure is hereby incorporated fully into the disclosure by this reference.

As used herein, the term "reversible bronchial obstruction" refers to a bronchial obstruction which is reversible at least partly by a bronchodilator, and includes asthma and its various clinical subsets (such as exercise induced asthma, nocturnal asthma, non-allergic asthma), chronic obstructive pulmonary disease, emphysema, chronic bronchitis, and cystic fibrosis, and any other lung disease where constricted bronchi can be dilated by agents such as β-agonists. A person of ordinary skill in the art will recognize that there are some patients which fail a one-time β-agonist reversibility test but nevertheless respond clinically to β-agonists with less shortness of breath and other symptoms, and are thus treated with these agents. All references to asthma and/or reversible bronchial obstructions are intended to include these conditions.

β-agonists are known to evoke bronchodilation by binding to airway smooth muscle $β_2$-adrenergic receptors ($β_2AR$). These receptors, members of the superfamily of 7-transmembrane (7-TM) receptors, carry out signal transduction by activating the heterotrimeric stimulatory guanine nucleotide binding protein ($G_s$), whose α subunit activates the effector adenylyl cyclase. Human airway smooth muscle expresses several isoforms of adenylyl cyclase, including types 5, 6 and 9. Their activation by $G_{αs}$ results in the catalytic conversion of ATP to cAMP, which subsequently activates the cAMP-dependent protein kinase PKA. This kinase phosphorylates multiple proteins in airway smooth muscle resulting in smooth muscle relaxation. See Genetics of Asthma, Marcel Dekker, Inc., New York, pp. 91-117 (1996).

Polymorphisms of the $β_2AR$ gene have been associated with the acute and chronic bronchodilation response to β-agonists. See, for example, Lima et al., Pharmacodynamics and Drug Action: Impact of genetic polymorphisms of the $β_2$-adrenergic receptor on albuterol bronchodilator pharmacodynamics. *Clin. Pharmacol. Ther.*, 65, 519-525 (1999). However, within such stratified populations there is still evidence for inter-individual variation, suggesting contributions of polymorphisms in other genes.

An additional aspect to β-agonist therapy is the apparent improvement in $β_2AR$ function in vitro, and β-agonist responsiveness in vivo, that occurs in the presence of corticosteroids. One mechanism of such interaction is the increase in cellular $β_2AR$ expression that occurs with corticosteroids. Studies utilizing direct stimulators of adenylyl cyclase have revealed increased catalytic activity in response to chronic corticosteroid treatment of cultured cells, though the mechanism of this phenomena has not been elucidated. Aksoy et al. "Glucocorticoid effects on the beta-adrenergic receptor-adenylyl cyclase system of human airway epithelium" *J. Allergy Clin. Immunol.*, 109, 491-497 (2002).

The nonsynonymous polymorphism of adenylyl cyclase type 9 (AC9) was previously identified by resequencing of the AC9 coding regions. The resequencing yielded only one nonsynonymous single nucleotide polymorphism (A2316G, Genbank accession number DQ008441), which results in a substitution of Ile for Met at amino acid 772. See, Small et al., "An Ile to Met polymorphism in the catalytic domain of adenylyl cyclase type 9 confers reduced $β_2$-adrenergic receptor stimulation" *Pharmacogenetics*, 13, 535-541 (2003), the disclosure of which is fully incorporated herein by this reference. The polymorphisms and the two different encoded proteins are heretofore referred to as either Met772 or Ile772.

Under standard culture conditions in stably transfected cells, Met772 exhibited a decreased catalytic activity. Surprisingly, however, cells expressing Met722 cultured in the presence of glucocorticoid had a significantly increased albuterol-stimulated adenylyl cyclase response (~800%) compared to those expressing Ile772 (~20%, P=0.02). An equivalent increase in $β_2AR$ expression was observed in both lines due to glucocorticoid, but AC9 expression was unaffected. Hence, the present inventor identified adenylyl cyclase type 9 (AC9) as a candidate for predicting β-agonist efficacy in the absence and presence of corticosteroid treatment.

The effects of a coding, nonsynonymous, polymorphism of AC9 on $β_2AR$ signaling in the absence and presence of corticosteroids in transfected cells in vitro, and in pediatric asthma patients who participated in a large clinical trial of inhaled corticosteroids was assessed. The present inventor determined this to be a pharmacogenetic locus for β-agonists in the treatment of asthma because of the relatively high allele frequency, the critical role that adenylyl cyclase plays in $β_2AR$ signal transduction, and based on previous in vitro studies showing an altered phenotype of Met772 compared to Ile772, (Small et al. Pharmacogenetics, 13, 535-541, supra). The present experiments and examples utilize A431 cells, which are a lung epidermoid carcinoma cell line. This line is chosen, in part, because of an observed increase in $β_2AR$ expression when these cells are exposed to dexamethasone (a synthetic adrenocortical steroid). Given that altered expression of proteins, such as the $β_2AR$, is part of the corticosteroid treatment effect in asthma, the A431 line is a preferred model system.

Hence, one embodiment of the present invention provides a pharmaceutical composition comprising an expression product of a Type Nine adenylyl cyclase (AC9) gene polymorphism and a physiologically acceptable carrier. In a more specific embodiment the expression product comprises AC9-Met722. Suitable routes of administration of pharmaceutical compositions intended to target the airway of a patient are known in the art. Non-limiting examples include inhalants and sprays. Another specific embodiment is directed to pharmaceutical compositions comprising an agent which increases an expression product of a Type Nine adenylyl cyclase gene polymorphism. In a very specific embodiment, the expression product comprises AC9-Met722.

The partial agonist albuterol is utilized to stimulate $β_2AR$ in the present in vitro studies, since albuterol is $β_2AR$ (as compared to β₁AR) selective, and is the same agent used in the clinical trial. Albuterol stimulated activities did not differ between WT and Met772 expressing cells in the absence of corticosteroid treatment. However, the increase in albuterol-stimulated activities evoked by exposure of the cells to dexamethasone was clearly higher for Met772 cells. With respect to the clinical study, there was no association observed between Met772 and the albuterol bronchodilator response in children with asthma who were randomized to the placebo group. However, in those receiving the inhaled corticosteroid budesonide, Met772 was associated with an increased bronchodilator response to albuterol compared to those with the WT AC9 genotype. The increase in bronchodilator response was statistically significant, as was the interaction between genotype and corticosteroid use. These clinical results are even more compelling when taken together with the in vitro data, which also showed a greater increase in the albuterol stimulated adenylyl cyclase response with Met772 under conditions of corticosteroid exposure.

Accordingly, another embodiment of the present invention provides a method of treating a patient having asthma or a reversible bronchial obstruction, the method comprising administering a pharmaceutical agent in conjunction with a treatment regimen comprising co-administration of at least one bronchodilator and at least one corticosteroid wherein the pharmaceutical agent comprises an expression product of a Type Nine adenylyl cyclase gene polymorphism or an agent which increases an expression product of a Type Nine adenylyl cyclase gene polymorphism. In a specific embodiment the at least one bronchodilator comprises a Beta2 agonist.

The current in vitro and clinical data are the opposite of what would have been predicted from previously published in vitro studies with this AC9 polymorphism, and thus these results represent novel findings. In a previous report, the polymorphic AC9 transfected into another cell type showed decreased $\beta_2$AR function. One would have expected, then, that the clinical response to the $\beta_2$AR agonist albuterol would be depressed in asthmatics. This expectation would be so regardless of corticosteroid treatment, since there was no evidence from prior work that there was a differential response in vitro to corticosteroids between Ile772 and Met772 AC9 protein. However, the present inventor surprisingly found that the Met772 AC9 polymorphism was associated with, and predicted, an increased response to albuterol in subject taking corticosteroids.

A further embodiment of the invention provides a method for treating a patient having asthma or a reversible bronchial obstruction, the method comprising (a) detecting a presence of the AC9-Met722 allelic variant in the patient; (b) identifying a patient who is a candidate for an effective treatment based on the presence of the AC9-Met722 allelic variant; and (c) administering the effective treatment. In a specific embodiment the effective treatment comprises co-administration of a selective $\beta_2$AR agonist and a corticosteroid.

The AC9-Met722 gene polymorphism noted herein is an SNP found at nucleotide 2316 where an A (wild-type) or G is noted, resulting in an Ile or Met at amino acid 772. The presence of a G in this portion creates unique BspHI restriction enzyme site at position 2312, allowing the existence of the base change to be detected by PCR amplification of a portion of the genomic DNA by subjecting it to digestion conditions with Bsp HI and 3% agarose gel electrophoresis. A cut (digest) indicates the presence of the G at position 2316. One may employ PCR amplification using the probe set forth in SEQ ID NO: 3 and the probe set forth in SEQ ID NO: 4 as primers, followed by digestion of the PCR product with BspH1. This technology can be exploited in the development of kits comprising means which enable detection of the presence or absence of the polymorphism, thus enabling a determination of a likelihood of a particular treatment regimen efficacy. A person of ordinary skill in the art will recognize, however, that, in addition to the techniques of PCR amplification and selective hybridization, there are many other techniques that are employable to detect the presence of an SNP in a nucleic acid sample. The scope of the invention is intended to include all such techniques, known and yet-to-be developed, which enable the detection of the AC9-Met722 gene polymorphism in a nucleic acid sample.

Primers for the detection PCR are: 5'-CTCTGTGCCTTG-GACTCCCCA-3' (sense) and 5'-TGGCCGCCTCGTACT-TCAGGA-3' (antisense), which provides for a 314 bp product. Reaction conditions consisted of approximately 100 ng genomic DNA, 5 pmol each primer, 0.8 mM dNTPs, 0.5 units of Platinum taq DNA polymerase and 4 µl 5× buffer D (Invitrogen) in a 20 µl volume. Incubations are at 94° C. for 4 min followed by 35 cycles of 94° C. for 30 s, 65° C. for 30 s, and 72° C. for 30 s, followed by a final extension at 72° C. for 7 minutes. Appropriate adaptations of these conditions to those suitable within the context of a kit are well-known and such adaptations will be readily apparent to a person of ordinary skill in the art.

Hence, kit embodiments for determination of whether an individual will be responsive to a treatment with a pharmaceutical agent are also provided. The kit comprises: at least one reagent specifically capable of detecting a presence of at least one polymorphism within a Type Nine adenylyl cyclase gene; and instructions for determining whether the individual will be responsive. In a specific embodiment the at least one polymorphism comprises an AC9-Met722 gene polymorphism. In another specific embodiment the presence is detected by detecting an expression product of the at least one polymorphism of a Type Nine adenylyl cyclase gene. In another specific embodiment the at least one reagent comprises a probe or primer which is capable of selectively hybridizing to a AC9 gene polymorphism segment as set forth in SEQ ID NO. 3 under stringent conditions, the probe or primer not being capable of selectively hybridizing under stringent conditions to a AC9 gene wild type segment as set forth in SEQ ID NO: 4. In a more specific embodiment the kit is adapted for rapid, on-sight determinations.

An assay embodiment is provided for screening pharmaceutical agents for efficacy in the treatment of asthma or reversible bronchial, obstruction. The assay comprises: measuring an amount of an expression product of an AC9 gene polymorphism and/or an amount of an expression product of a $\beta_2$AR gene in the presence of a pharmaceutical agent with a corticosteroid; measuring an amount of an expression product of an AC9 gene polymorphism and/or an amount of an expression product of a $\beta_2$AR gene in the presence of a pharmaceutical agent without a corticosteroid; identifying an effective pharmaceutical agent. In one specific embodiment of the assay, an increase in the amount measured in (a) relative to the amount measured in (b) indicates greater efficacy.

The invention additionally provides embodiments directed to a method for predicting the response to treatment with a YEAR agonist in a patient having asthma or a reversible bronchial obstruction wherein the patient is taking at least one corticosteroid. The method comprises: detecting an AC9 gene polymorphism or an expression product thereof in the patient. In a specific embodiment, the AC9 gene polymorphism is detected by a probe or primer which is capable of selectively hybridizing to the AC9 gene polymorphism segment as set forth in SEQ ID NO: 3 under stringent conditions, the probe or primer not being capable of selectively hybridizing under stringent conditions to the AC9 gene wild type segment as set forth in SEQ ID NO: 4. A non-limiting example of a suitable probe for Ile722 comprises 5'-AGGTCAGAAAGAACT-3' (SEQ ID NO: 4) and a non-limiting example of a suitable probe for Met772 comprises 5'-AGGTCAGGAAGAACT-3' (SEQ ID NO: 3). In another specific embodiment the expression product is AC9-Met722.

SNPs of the $\beta_2AR$ gene have been shown to be associated with certain $\beta$-agonist phenotypes. The present inventor considered that they may act in an additive or other epistatic fashion with the AC9 Met772 polymorphism. While an analyses of the current cohort evaluating whether SNPs at nucleotide positions 46 (or 79) and 523 in the coding exon the $\beta_2AR$ gene significantly modify the association of the AC9 Met772 polymorphism yielded no evidence for epistasis, a haplotypic analyses yielded more insight into these relationships. A strong interaction between $\beta_2AR$ haplotype, AC9 Met772, corticosteroid use, and the albuterol bronchodilator response was found. To the knowledge of the present inventor, this represents the first reported 2-gene, 2-drug interaction in asthma pharmacogenetic studies to date. This epistasis may be simply additive, or potentially synergistic.

A further embodiment provides a method for determining whether a patient having asthma or a reversible bronchial obstruction will be responsive to a particular treatment regimen. The method comprises: (a) detecting and identifying an AC9 gene polymorphism; (b) detecting and identifying a $\beta_2AR$ haplotype; (c) determining a pharmacogenetic profile index based on (a) and (b); (d) correlating the pharmacogenetic profile index with efficacy of the particular treatment regimen.

The AC9 Met772 polymorphism is associated with a glucocorticoid-specific upregulation of the bronchodilatory response both in transfected lung cells and in childhood asthmatics. It is anticipated that this will be the case for sufferers of other forms of reversible bronchial obstruction where the mechanism of obstruction is similar. That this response is specific to treatment with glucocorticoids lends further insight into the mechanisms behind the molecular interactions of the corticosteroid and $\beta$-adrenergic pathways. Albuterol remains the most commonly employed medication in the acute therapy of asthma (and is often used for chronic control as well), and inhaled glucocorticoids are prescribed as long-term "controller" agents for asthma. Thus these findings are directly relevant to the community management of asthma, since this is a common two-drug treatment regimen. Along with polymorphisms of the $\beta_2AR$ gene, the polymorphism in the AC9 gene represents a second pharmacogenomic locus that has predictive potential for $\beta$-agonist responsiveness. The discovery of multiple such loci enables the ranking and calculation of a composite pharmacogenetic index which provides increasing predictive power for clinical guidance of therapy.

The following examples are intended to illustrate certain aspects of the invention and are not intended to limit the scope in any way.

EXAMPLES

In the following examples, the in vitro and in vivo phenotypes of a nonsynonymous polymorphism of adenylyl cyclase type 9 are examined. Specifically, signal transduction of the two AC9s in a transfected lung cell line in the absence and presence of corticosteroid treatment are illustrated by determination of adenylyl cyclase activities in response to $\beta_2AR$ stimulation. In the second Example, a large placebo-controlled clinical trial of the corticosteroid budesonide in pediatric asthmatics is conducted, and associations between the AC9 polymorphism and $\beta$-agonist responsiveness are demonstrated. Based on the previously reported association of SNPs and haplotypes of the $\beta_2AR$ gene with the degree of bronchodilator response the influence of these SNPs and haplotypes on bronchodilator response in relation to Met772 status is also assessed. See, e.g., Silverman et al. Family-based association analysis of beta2-adrenergic receptor polymorphisms in the childhood asthma management program. *J. Allergy Clin. Immunol.*, 112, 870-876 (2003), and Israel, et al. "Use of regularly scheduled albuterol treatment in asthma: genotype-stratified, randomised, placebo-controlled cross-over trial" *The Lancet*, 364, 1505-1512 (2004), incorporated herein by reference. Taken together results demonstrate that, in vitro, the Met772 polymorphism of AC9 imparts enhanced $\beta_2AR$ signal transduction in a corticosteroid-specific manner, and, in human asthma the polymorphism is associated with enhanced $\beta$-agonist bronchodilator response under circumstances when corticosteroids are co-administered.

In the clinical study, the hypothesis being tested is that Met772 AC9 is associated with an improved albuterol bronchodilator response in asthmatics. Subjects include 436 asthmatic children who were followed for 4 years, and were randomized to receive placebo or the inhaled corticosteroid budesonide. Met772 carriers on budesonide showed a significant improvement in $FEV_1$ (P=0.005). Moreover, a highly significant interaction (P=0.002) was found for budesonide treatment and the AC9 polymorphism. These in vitro and human association studies are consistent with this AC9 polymorphism altering albuterol responsiveness in the context of concomitant inhaled corticosteroid administration, which is a common asthma regimen. The Met772 AC9 polymorphism represents one, of most likely several, multi-gene polymorphisms along the receptor-relaxation axis, which together may provide for a composite pharmacogenetic index for asthma therapy.

Materials and Methods
Transfections and Cell Culture

The WT coding sequence for the human AC9 gene is considered that of GenBank accession number DQ005545. With the adenine of the initiator codon being considered nucleotide 1, a polymorphism consisting of an A>G transition at nucleotide 2316 which results in substitution of Ile with Met at amino acid position 772 (accession number DQ008441) was previously described in Small et al, *Pharmacogenetics*, 13, 535-541, supra. The cDNAs for Ile772 (also referred to as WT) and Met772 coding regions were generated from human lymphocyte RNA, subcloned into pCNDA3, and transfections of A431 cells carried out as described. Selection of positive clones was carried out in media containing 400 μg/ml G418. Expression of AC9 was determined in individual clonal lines by Western blots (see below). A431 cells were grown in monolayers in Dulbecco's modified Eagle's medium with 4 mM L-glutamate 10% fetal bovine serum, 100 U/ml penicillin and 100 μg/ml streptomycin, at 37° in a 5% $CO_2$ atmosphere. In some studies, cells at 90% confluency in the absence of serum were treated with 500 nM dexamethasone for 12 hours and then utilized as described below.

Radioligand Binding and Western Blots

Transfected A431 cells were washed three times with phosphate-buffered saline (PBS), detached by scraping in 5 mM Tris, pH 7.4, 2 mM ethylenediaminetetracetic acid (EDTA) buffer, and centrifuged at 30,000 g for 10 min. To determine endogenous $\beta_2AR$ density, membrane pellets were resuspended in 75 mM Tris, pH 7.4, 12.5 mM $MgCl_2$, 2 mM EDTA, and radioligand binding with $^{125}$I-cyanopindolol was performed as described in Mialet-Perez et al., "A primate-dominant third glycosylation site of the Beta2-adrenergic receptor routes receptors to degradation during agonist regulation." *J. Biol. Chem.*, 279. 38603-38607 (2004). Nonspecific binding was determined with 1 µM propranolol. Reactions were carried out for 2 hours at 25° C., terminated by 5 dilution, and bound radioligand separated by vacuum filtration. AC9 expression in these transfected cell lines was assessed by quantitative immunoblotting so as to select lines expressing Ile772 or Met772 at the same levels for pharmacologic studies, and to ascertain if corticosteroid treatment altered expression. Confluent cells were washed three times with PBS and then lysed in RIPA buffer (PBS containing 1% Igepal CA-630, 0.5% deoxycholate, 0.1% SDS) with protease inhibitors (10 µg/ml benzamidine, 10 µg/ml soybean trypsin inhibitor, 10 µg/ml aprotinin and 5 µg/ml leupeptin). Western blots of these whole cell lysates were performed by enhanced chemiluminescence as previously described, using an isoform-specific polyclonal AC9 antibody (obtained from R. Premont, Duke University) at a dilution of 1:2000. Relative levels of AC9 expression were subsequently determined using ScanAnalysis software (BioSoft, Cambridge, UK).

Adenylyl Cyclase Activities

Cell membranes prepared as above were incubated with 30 mmol Tris, pH 7.4, 2 mM $MgCl_2$, 0.8 mM EDTA, 120 µM ATP, 60 µM GTP, 2.8 mM phosphoenolpyruvate, 50 µg/ml myokinase, 4 U/ml pyruvate kinase, 100 µM cAMP and 1 µCi of $[\alpha-^{32}P]ATP$ for 15 min as described in Perez, J. M et al., "$Beta_1$-adrenergic receptor polymorphisms confer differential function and predisposition to heart failure" *Nat. Med.*, 9, 1300-1305 (2003). The reactions were incubated in the presence of vehicle (basal), 10 µM albuterol, 1.8 mM $MnCl_2$ or 10 mM NaF. $[^{32}P]$ cAMP was separated from $[\alpha-^{32}P]$ by chromatography over alumina columns. The $[^{3}H]$ cAMP standard included in the stop buffer accounted for individual column recovery.

Patient Population

The study cohort consisted of pediatric patients who participated in the Childhood Asthma Management Program (CAMP). The study was a multicenter, randomized, trial comparing regularly scheduled inhalation treatment with the corticosteroid budesonide, the putative mast-cell "stabilizer" nedocromil, and placebo. The study design has been previously published in "Long-term effects of budesonide or nedocromil in children with asthma" *N. Engl. J. Med.*, 343, 1054-1063 (2000). Briefly, children were enrolled between the ages of 5-12 years of age (mean age of asthma onset was 3.1 years) and followed for 4-6 years. Eighty-three percent of these children were classified as atopic, based on at least one positive skin test. Spirometry was performed twice yearly, before and after the administration of a standard dose of the β-agonist bronchodilator albuterol. Once per year a methacholine challenge was performed to ascertain bronchial hyperresponsiveness. The current study utilized archived DNA from patients who participated in the CAMP DNA Ancillary Study. Because of potential population stratification issues (the allele frequency of Met772 is ~0.30 in Caucasians and ~0.15 in African Americans) and the small number of African American children enrolled in CAMP (14%), the current study was confined to Caucasian children. Moreover, since the effects of nedocromil on bronchodilator response have not been biologically characterized, this treatment arm was excluded from the analysis. The analysis was focused then, on 436 children, with follow-up through 48 months, the last time point in which nearly complete measures were obtained for the cohort. The subjects' parents provided informed consent, and the study was approved by the Institutional Review Boards of each participating center.

Genotyping

The AC9 SNP at nucleotide 2316 was genotyped via a SEQUENOM MassARRAY MALDI-TOF mass spectrometer (Sequenom, San Diego, Calif.) for analysis of unlabeled single-base extension minisequencing reactions with a semi-automated primer design program (SpectroDESIGNER, Sequenom). The protocol implemented the very short extension method whereby sequencing products are extended by only one base for 3 of the 4 nucleotides and by several additional bases for the fourth nucleotide (representing one of the alleles for a given SNP), permitting clearly delineated mass separation of the two allelic variants at a given locus. $β_2AR$ SNPs at positions −709, −654, −47, 46, 79, 252, 491 and 523 (see Drysdale et al., "Complex promoter and coding region Beta-2 adrenergic receptor haplotypes alter receptor expression and predict in vivo responsiveness," *Proc. Natl. Acad. Sci.* U.S.A., 97, 10483-10488 (2000)) were determined using similar methods as previously described in Silverman, et al., "Family-based association analysis of beta2-adrenergic receptor polymorphisms in the childhood asthma management program," *J. Allergy Clin. Immunol.*, 112, 870-876 (2003). To assess for possible population stratification, a random panel of 49 SNPs across the genome ("stratification SNPs"), obtained through the SNP Consortium (TSC) database, was also genotyped. SNPs were chosen that are widely distributed throughout the genome and exclude promoters, genomic UTRs, exons, and introns of known genes.

Statistical Analysis

Bronchodilator response is defined as $FEV_1$ after bronchodilator minus $FEV_1$ before bronchodilator divided by $FEV_1$ before bronchodilator times 100 [(Post-$FEV_1$−Pre-$FEV_1$)/(Pre-$FEV_1$)×100]. Longitudinal models of bronchodilator response, using repeated measures modeling with time as a linear effect and an unstructured covariance matrix, are used. These models evaluate change in bronchodilator response beginning at the 2 month follow-up visit, allowing for evaluation of change based on treatment type. Univariate and multivariable analyses adjusting for age, sex, and bronchodilator response at baseline are performed, under the assumption of a dominant model. To test for interaction between steroid treatment and Ile772Met genotypic status, treatment specific strata was evaluated and included interaction terms in the models. A "mean bronchodilator" response is also derived by taking all of the observations over the 4 years and dividing by the number of visits. This value was used as the primary outcome in the haplotypic assessment of interactions between the $β_2AR$ locus and the AC9 polymorphism.

The potential for epistasis between the $β_2AR$ gene and the Met772 variant is explored in relation to both individual SNPs and haplotypes. Eight $β_2AR$ SNPs were evaluated, as previously reported; these were encoded in an additive fashion. Individual SNP analyses followed the within-treatment group repeated measures analyses outlined above with the addition of a SNP by Met772 interaction term. $β_2AR$ haplotypes were analyzed using the haplo.score function from the haplo.stats package (Version 1.1.0. Mayo Clinic, Rochester, Minn.). The global association of the $β_2AR$ haplotypes with mean bronchodilator response over the 4 year trial period was evaluated for the entire cohort initially, then stratified by Met772 status. Finally, these analyses were further stratified by treatment arm and Met772 status.

Analysis of the stratification SNPs proceeded in two steps. First, for each individual SNP, an allelic $\chi^2$ test statistic was obtained in standard fashion, utilizing 2×2 contingency tables that allocated the totals of the wild-type and variant alleles for the highest and lowest quartiles of mean bronchodilator response to each of 4 cells. An overall summary $\chi^2$ test statistic was then obtained by summing the individual $\chi^2$ test statistics, setting the degrees of freedom to the number of tests. This analysis was performed using SAS (Version 8, Cary, N.C.).

Results

AC9-Met772 Phenotype in A431 Cells

Figure 2:
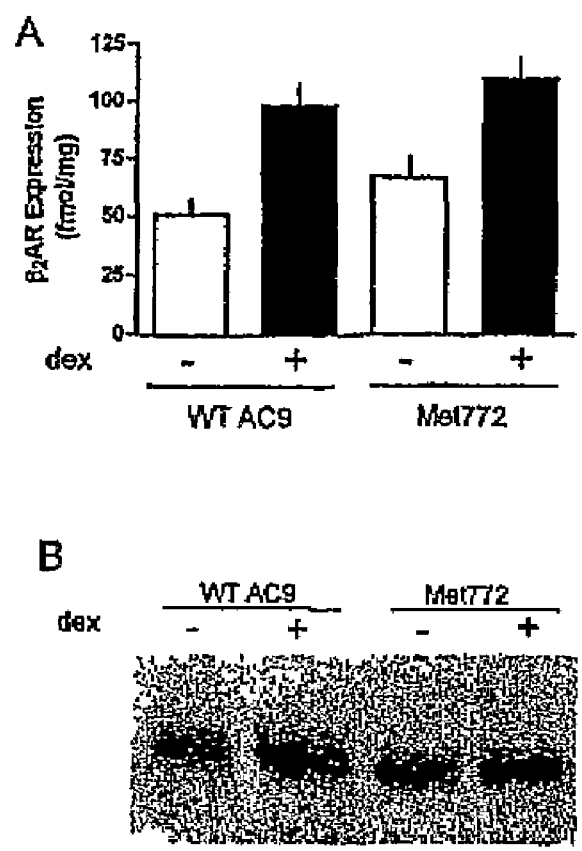
FIG. 2. Effects of corticosteroid treatment of transfected A431 cells on $β_2AR$ and AC9 expression. In A), results from $^{125}$I-CYP radioligand studies show that cells expressing WT and Met772 AC9 both displayed an equivalent increase in $β_2AR$ expression after 12 hours of exposure to dexamethasone (dex). Results are from 5 experiments. * P<0.01 compared to absence of dexamethasone. In B), a representative Western blot of AC9 shows that dexamethasone treatment did not increase expression of either AC9 allelic variants in these cells.
Figure 3:
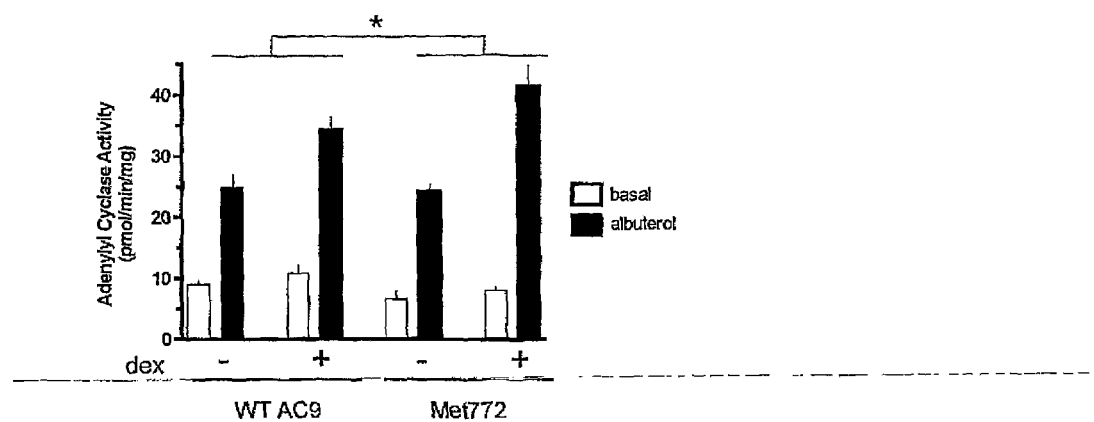
FIG. 3. Effects of corticosteroid treatment of transfected A431 cells on albuterol-stimulated adenylyl cyclase activities. The increase in albuterol-stimulated activities from dexamethasone (dex) treatment was greater for Met772 expressing cells vs WT, compared as either the absolute activities (P=0.02) or the fold increase over basal (P=0.006). *, significant as defined above.

Stably transfected cell lines were screened by Western blots to identify lines expressing equivalent levels of WT and Met772 AC9. Two lines expressing each genotype were chosen for further study. The signaling characteristics of WT and Met772 AC9 are shown in FIG. 1. Basal adenylyl cyclase activities, as well as those stimulated by the partial agonist albuterol, were not different between the lines. The most prominent feature was the decreased catalytic activity of Met772 as assessed by stimulation with NaF (which stimulates by activating $G_{\alpha s}$) and $MnCl_2$ (which directly activates adenylyl cyclase). Met772 activities under these conditions were decreased compared to WT. (Of note, AC9 is not stimulated by forskolin.) The endogenous $\beta_2AR$ expression, as determined by $^{125}I$-CYP radioligand binding, was not different between the two lines (WT=51±6.2 vs Met772=66±8.9 fmol/mg). We next explored the phenotypes under conditions of 24 hrs of corticosteroid exposure. As expected, $\beta_2AR$ expression increased in both lines (to 103±7.8 and 109±9.0 fmol/mg, respectively); however, the expression of WT AC9 or the variant was not changed by dexamethasone treatment (FIG. 2). The effects of dexamethasone treatment on basal and albuterol-stimulated adenylyl cyclase activities are shown in FIG. 3. As can be seen, the corticosteroid increased albuterol stimulated activities to a greater extent in the Met772 cells compared to WT (24±1.3 to 43±3.4 vs 27±2.1 to 33±2.5 pmol/min/mg, respectively, N=5, P=0.02). This was also the case when one considers the fold-increase in activities over basal promoted by albuterol. In the presence of dexamethasone, these values were 4.9±0.60 vs 3.2±0.36 fold, respectively, P=0.006. Using another set of clonal cell lines, these values were 4.6±0.45 fold for Met772 and 2.9±0.11 fold for WT AC9 (P=0.02). Taken together, then, albuterol responsiveness was found to be greater in cells expressing the Met772 AC9 as compared to WT AC9, but only in the presence of corticosteroid.

AC9-Met772 Associates with Enhanced Bronchodilation

The relationship between this AC9 polymorphism and β-agonist promoted bronchodilation was assessed by genotyping a subset of patients who had been enrolled in the CAMP study (see Above). The baseline clinical characteristics of these patients stratified by genotype is shown in Table 1. There were no differences in these parameters between those with or without Met772. In particular, bronchodilator response, airway hyperresponsiveness (as manifested by $PC_{20}$), $FEV_1\%$ predicted, FVC % predicted, and the $FEV_1/FVC$, were not different amongst the groups at randomization.

TABLE 1

Baseline Characteristics of Patients Stratified by the AC9 Polymorphism

|  | WT | Met772 carrier |
| --- | --- | --- |
| Number | 222 | 214 |
| Age | 8.75 ± 2.17 | 8.88 ± 2.11 |
| Gender (% male) | 128 (57.7) | 123 (57.5) |
| Randomized to Steroids (%) | 88 (39.6) | 89 (41.6) |
| Pre-bronehodilator $FEV_1$ % pred | 95.31 ± 14.23 | 94.63 ± 14.03 |
| Pre-bronchodilator FVC % pred | 105.44 ± 13.94 | 105.38 ± 12.57 |

TABLE 1-continued

Baseline Characteristics of Patients Stratified by the AC9 Polymorphism

|  | WT | Met772 carrier |
| --- | --- | --- |
| Pre-bronchodilator $FEV_1/FVC$ | 80.08 ± 7.91 | 79.50 ± 8.58 |
| Post-bronchodilator $FEV_1$ % pred | 104.42 ± 13.12 | 104.26 ± 12.01 |
| Post-bronchodilator FVC % pred | 107.31 ± 13.09 | 108.05 ± 12.64 |
| Post-bronchodilator $FEV_1/FVC$ | 86.18 ± 6.19 | 85.47 ± 6.75 |
| Log $PC_{20}$ | 0.02 ± 1.15 | 0.06 ± 1.19 |
| Bronchodilator response | 10.32 ± 9.18 | 11.17 ± 11.24 |

Figure 4:
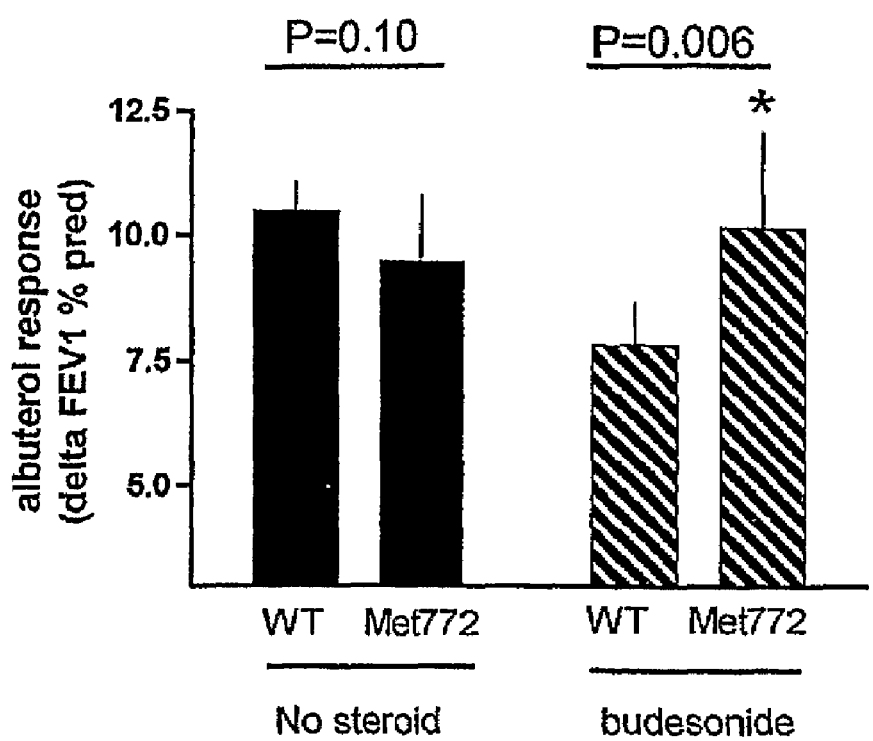
FIG. 4. Interaction between corticosteroid treatment, AC9 genotype, and β-agonist bronchodilation in asthmatics. Results are from the clinical cohort as described in Methods, showing the average bronchodilator response over the 4 year follow-up period. Met772 patients experienced an improvement in bronchodilator response only if they were being treated with budesonide (P=0.006). The interaction P value for genotype and budesonide treatment is 0.002.

The results from analysis of the primary outcome variable, the β-agonist bronchodilator response over a 4 year follow-up period are shown in Table 2. The univariate models revealed no discernable differences in bronchodilator response over time for the overall cohort. Moreover, while there was no significant difference in the bronchodilator response over time in individuals with varying genotypes on placebo (P=0.21), the Met772 carriers on the inhaled corticosteroid budesonide demonstrated approximately a 2 percentage point increase in bronchodilation response when compared to wild type (6.76±0.69 vs 8.72±0.54, P=0.005). There was a significant interaction noted for the use of inhaled steroids in combination with Met772 carrier status (interaction P=0.002). Even after adjusting for age, gender, and baseline bronchodilator response, those on inhaled corticosteroids with the variant genotype still demonstrated significant increases in bronchodilator response compared to wild type (P=0.04), while those on placebo did not. The interaction P-value for use of budesonide and Met772 is 0.03 with this analysis. These relationships are further demonstrated graphically by plotting average bronchodilator response over the 4 year follow-up period by genotype and treatment status (FIG. 4). Analysis of the stratification SNPs revealed no evidence of population stratification for the entire cohort or for either treatment group alone; all P-values were >0.05 for the highest vs. the lowest mean bronchodilator quartiles (data not shown).

The potential for epistasis between $\beta_2AR$ SNPs and haplotypes with the Met772 variant was examined, using eight $\beta_2AR$ SNPs previously reported. No significant interactions between any individual $\beta_2AR$ SNP and the Met772 variant was noted (data not shown). However, the power to detect such an association was relatively low. For instance, in the Caucasian children who carried Met772, and who were on inhaled corticosteroids, only 3 were homozygous for the SNP at position 523. Since it has previously been shown that haplotypes within the $\beta_2AR$ gene may have more power to detect phenotypic outcomes, the focus of the remainder of the analyses was on the potential for effect modification of the $\beta_2AR$ haplotypes by Met772 on bronchodilator outcomes.

Using multivariable models in haplo.score, global P-values of association between $\beta_2AR$ haplotypes and mean bronchodilator response were evaluated, with and without stratification by Met772 status and treatment group assignment. For the entire cohort, $\beta_2AR$ haplotypes were nominally associated with mean bronchodilator response (P=0.05). After subsetting by AC9 genotype status alone, $\beta_2AR$ haplotypes in the Ile772 group were not associated with bronchodilator response (P=0.34). However, in those individuals with at least one Met772 allele, a modest association with $\beta_2AR$ haplotypes and bronchodilator response was observed (P=0.03). Most notably, the global association of $\beta_2AR$ haplotypes with bronchodilator response was particularly strong for the Met772 subgroup who were randomized to inhaled corticosteroids (P<0.001).

TABLE 2

Longitudinal Bronchodilator Response in CAMP, Stratified by Met772 Genotype*

| | Univariate | | | Multivariate[†] | | |
|---|---|---|---|---|---|---|
| | Wildtype | Met772 | p-value | Wildtype | Met772 | p-value |
| Overall Cohort | 9.41 ± 0.48 | 9.23 ± 0.34 | 0.71 | 6.45 ± 0.40 | 6.17 ± 0.92 | 0.48 |
| Placebo Group | 10.92 ± 0.79 | 9.94 ± 0.61 | 0.21 | 6.99 ± 0.60 | 6.77 ± 1.38 | 0.70 |
| Steroid Group[††] | 6.76 ± 0.69 | 8.72 ± 0.54 | 0.005 | 4.52 ± 0.64 | 5.78 ± 1.49 | 0.04 |

*Values shown represent the average bronchodilator response (Post-bronchodilator $FEV_1$-Pre-bronchodilator $FEV_1$)/(Pre-bronchodiltor $FEV_1$) in percent (±SE) for a given genotype and treatment group status.
[†]Adjusted for age, gender, inhaled steroid usage, baseline bronchodilator response, and time for the entire cohort and for age, gender, baseline bronchodilator response and time for the treatment stratified analyses.
[††]Interaction p-value between steroid usage and Met772 Genotype was 0.002 for the univariate and 0.03 for the multivariate analyses.

---

What is claimed is:

1. A method for predicting an increased response to treatment with a $\beta_2 AR$ agonist compared to a wild type response in a patient having asthma or a reversible bronchial obstruction wherein the patient is taking at least one corticosteroid, the method comprising: detecting a Met772 polymorphism in the coding region of a type nine adenylyl cyclase gene or an expression product thereof in the patient, wherein presence of the Met772 polymorphism indicates an increased response to treatment with a $\beta_2 AR$ agonist compared to the wild type response in the patient.

2. The method as recited in claim 1 wherein the polymorphism is detected by a probe or primer which is capable of selectively hybridizing to the type nine adenylyl cyclase gene polymorphism segment as set forth in SEQ ID NO: 2 but not to a type nine adenylyl cyclase gene wild type segment.

* * * * *

UNITED STATES PATENT AND TRADEMARK OFFICE
CERTIFICATE OF CORRECTION

| | | Page 1 of 1 |
|---|---|---|
| PATENT NO. | : 8,071,287 B2 | |
| APPLICATION NO. | : 11/912205 | |
| DATED | : December 6, 2011 | |
| INVENTOR(S) | : Liggett | |

It is certified that error appears in the above-identified patent and that said Letters Patent is hereby corrected as shown below:

In the specification

Col. 1 line 8, insert,

--FEDERALLY SPONSORED RESEARCH OR DEVELOPMENT

This invention was developed at least in part pursuant to the United States government support of Grant No. U01 HL065899, awarded by the National Institutes of Health. The United States government has certain rights therein.--

Signed and Sealed this
Sixth Day of October, 2015

Michelle K. Lee
*Director of the United States Patent and Trademark Office*

SEQUENCE LISTING

<160> NUMBER OF SEQ ID NOS: 4

<210> SEQ ID NO 1
<211> LENGTH: 1353
<212> TYPE: PRT
<213> ORGANISM: human

<400> SEQUENCE: 1

```
Met Ala Ser Pro Pro His Gln Gln Leu Leu His His His Ser Thr Glu
1               5                   10                  15

Val Ser Cys Asp Ser Ser Gly Asp Ser Asn Ser Val Arg Val Lys Ile
            20                  25                  30

Asn Pro Lys Gln Leu Ser Ser Asn Ser His Pro Lys His Cys Lys Tyr
        35                  40                  45

Ser Ile Ser Ser Ser Cys Ser Ser Gly Asp Ser Gly Gly Val Pro
    50                  55                  60

Arg Arg Val Gly Gly Gly Gly Arg Leu Arg Arg Gln Lys Lys Leu Pro
65                  70                  75                  80

Gln Leu Phe Glu Arg Ala Ser Ser Arg Trp Trp Asp Pro Lys Phe Asp
                85                  90                  95

Ser Val Asn Leu Glu Glu Ala Cys Leu Glu Arg Cys Phe Pro Gln Thr
            100                 105                 110

Gln Arg Arg Phe Arg Tyr Ala Leu Phe Tyr Ile Gly Phe Ala Cys Leu
        115                 120                 125

Leu Trp Ser Ile Tyr Phe Ala Val His Met Arg Ser Arg Leu Ile Val
    130                 135                 140

Met Val Ala Pro Ala Leu Cys Phe Leu Leu Val Cys Val Gly Phe Phe
145                 150                 155                 160

Leu Phe Thr Phe Thr Lys Leu Tyr Ala Arg His Tyr Ala Trp Thr Ser
                165                 170                 175

Leu Ala Leu Thr Leu Leu Val Phe Ala Leu Thr Leu Ala Ala Gln Phe
            180                 185                 190

Gln Val Leu Thr Pro Val Ser Gly Arg Gly Asp Ser Ser Asn Leu Thr
        195                 200                 205

Ala Thr Ala Arg Pro Thr Asp Cys Leu Ser Gln Val Gly Ser Phe
    210                 215                 220

Ser Met Cys Ile Glu Val Leu Phe Leu Leu Tyr Thr Val Met His Leu
225                 230                 235                 240
```

```
Pro Leu Tyr Leu Ser Leu Cys Leu Gly Val Ala Tyr Ser Val Leu Phe
                245                 250                 255

Glu Thr Phe Gly Tyr His Phe Arg Asp Glu Ala Cys Phe Pro Ser Pro
            260                 265                 270

Gly Ala Gly Ala Leu His Trp Glu Leu Leu Ser Arg Gly Leu Leu His
        275                 280                 285

Gly Cys Ile His Ala Ile Gly Val His Leu Phe Val Met Ser Gln Val
    290                 295                 300

Arg Ser Arg Ser Thr Phe Leu Lys Val Gly Gln Ser Ile Met His Gly
305                 310                 315                 320

Lys Asp Leu Glu Val Glu Lys Ala Leu Lys Arg Met Ile His Ser
                325                 330                 335

Val Met Pro Arg Ile Ile Ala Asp Asp Leu Met Lys Gln Gly Asp Glu
            340                 345                 350

Glu Ser Glu Asn Ser Val Lys Arg His Ala Thr Ser Ser Pro Lys Asn
        355                 360                 365

Arg Lys Lys Lys Ser Ser Ile Gln Lys Ala Pro Ile Ala Phe Arg Pro
    370                 375                 380

Phe Lys Met Gln Gln Ile Glu Glu Val Ser Ile Leu Phe Ala Asp Ile
385                 390                 395                 400

Val Gly Phe Thr Lys Met Ser Ala Asn Lys Ser Ala His Ala Leu Val
            405                 410                 415

Gly Leu Leu Asn Asp Leu Phe Gly Arg Phe Asp Arg Leu Cys Glu Glu
        420                 425                 430

Thr Lys Cys Glu Lys Ile Ser Thr Leu Gly Asp Cys Tyr Tyr Cys Val
    435                 440                 445

Ala Gly Cys Pro Glu Pro Arg Ala Asp His Ala Tyr Cys Cys Ile Glu
    450                 455                 460

Met Gly Leu Gly Met Ile Lys Ala Ile Glu Gln Phe Cys Gln Glu Lys
465                 470                 475                 480

Lys Glu Met Val Asn Met Arg Val Gly Val His Thr Gly Thr Val Leu
            485                 490                 495

Cys Gly Ile Leu Gly Met Arg Arg Phe Lys Phe Asp Val Trp Ser Asn
        500                 505                 510

Asp Val Asn Leu Ala Asn Leu Met Glu Gln Leu Gly Val Ala Gly Lys
    515                 520                 525

Val His Ile Ser Glu Ala Thr Ala Lys Tyr Leu Asp Asp Arg Tyr Glu
    530                 535                 540

Met Glu Asp Gly Lys Val Ile Glu Arg Leu Gly Gln Ser Val Val Ala
545                 550                 555                 560

Asp Gln Leu Lys Gly Leu Lys Thr Tyr Leu Ile Ser Gly Gln Arg Ala
            565                 570                 575

Lys Glu Ser Arg Cys Ser Cys Ala Glu Ala Leu Leu Ser Gly Phe Glu
        580                 585                 590

Val Ile Asp Gly Ser Gln Val Ser Ser Gly Pro Arg Gly Gln Gly Thr
    595                 600                 605

Ala Ser Ser Gly Asn Val Ser Asp Leu Ala Gln Thr Val Lys Thr Phe
    610                 615                 620

Asp Asn Leu Lys Thr Cys Pro Ser Cys Gly Ile Thr Phe Ala Pro Lys
625                 630                 635                 640

Ser Glu Ala Gly Ala Glu Gly Gly Ala Pro Gln Asn Gly Cys Gln Asp
            645                 650                 655

Glu His Lys Asn Ser Thr Lys Ala Ser Gly Gly Pro Asn Pro Lys Thr
        660                 665                 670
```

```
Gln Asn Gly Leu Leu Ser Pro Pro Gln Glu Glu Lys Leu Thr Asn Ser
            675                 680                 685

Gln Thr Ser Leu Cys Glu Ile Leu Gln Glu Lys Gly Arg Trp Ala Gly
        690                 695                 700

Val Ser Leu Asp Gln Ser Ala Leu Leu Pro Leu Arg Phe Lys Asn Ile
705                 710                 715                 720

Arg Glu Lys Thr Asp Ala His Phe Val Asp Val Ile Lys Glu Asp Ser
            725                 730                 735

Leu Met Lys Asp Tyr Phe Phe Lys Pro Pro Ile Asn Gln Phe Ser Leu
            740                 745                 750

Asn Phe Leu Asp Gln Glu Leu Glu Arg Ser Tyr Arg Thr Ser Tyr Gln
            755                 760                 765

Glu Glu Val Met Lys Asn Ser Pro Val Lys Thr Phe Ala Ser Pro Thr
        770                 775                 780

Phe Ser Ser Leu Leu Asp Val Phe Leu Ser Thr Thr Val Phe Leu Thr
785                 790                 795                 800

Leu Ser Thr Thr Cys Phe Leu Lys Tyr Glu Ala Ala Thr Val Pro Pro
            805                 810                 815

Pro Pro Ala Ala Leu Ala Val Phe Ser Ala Ala Leu Leu Glu Val
            820                 825                 830

Leu Ser Leu Ala Val Ser Ile Arg Met Val Phe Phe Leu Glu Asp Val
            835                 840                 845

Met Ala Cys Thr Lys Arg Leu Leu Glu Trp Ile Ala Gly Trp Leu Pro
        850                 855                 860

Arg His Cys Ile Gly Ala Ile Leu Val Ser Leu Pro Ala Leu Ala Val
865                 870                 875                 880

Tyr Ser His Val Thr Ser Glu Tyr Glu Thr Asn Ile His Phe Pro Val
            885                 890                 895

Phe Thr Gly Ser Ala Ala Leu Ile Ala Val Val His Tyr Cys Asn Phe
            900                 905                 910

Cys Gln Leu Ser Ser Trp Met Arg Ser Ser Leu Ala Thr Val Val Gly
            915                 920                 925

Ala Gly Pro Leu Leu Leu Tyr Val Ser Leu Cys Pro Asp Ser Ser
        930                 935                 940

Val Leu Thr Ser Pro Leu Asp Ala Val Gln Asn Phe Ser Ser Glu Arg
945                 950                 955                 960

Asn Pro Cys Asn Ser Ser Val Pro Arg Asp Leu Arg Arg Pro Ala Ser
            965                 970                 975

Leu Ile Gly Gln Glu Val Val Leu Val Phe Phe Leu Leu Leu Leu Leu
            980                 985                 990

Val Trp Phe Leu Asn Arg Glu Phe  Glu Val Ser Tyr Arg  Leu His Tyr
            995                1000                1005

His Gly  Asp Val Glu Ala Asp  Leu His Arg Thr Lys  Ile Gln Ser
    1010                1015                1020

Met Arg  Asp Gln Ala Asp Trp  Leu Leu Arg Asn Ile  Ile Pro Tyr
    1025                1030                1035

His Val  Ala Glu Gln Leu Lys  Val Ser Gln Thr Tyr  Ser Lys Asn
    1040                1045                1050

His Asp  Ser Gly Gly Val Ile  Phe Ala Ser Ile Val  Asn Phe Ser
    1055                1060                1065

Glu Phe  Tyr Glu Glu Asn Tyr  Glu Gly Gly Lys Glu  Cys Tyr Arg
    1070                1075                1080

Val Leu  Asn Glu Leu Ile Gly  Asp Phe Asp Glu Leu  Leu Ser Lys
```

-continued

|                  | 1085             |                  | 1090             |                  | 1095             |
| --- | --- | --- | --- | --- | --- |

Pro Asp Tyr Ser Ser Ile Glu Lys Ile Lys Thr Ile Gly Ala Thr
1100                1105                1110

Tyr Met Ala Ala Ser Gly Leu Asn Thr Ala Gln Ala Gln Asp Gly
1115                1120                1125

Ser His Pro Gln Glu His Leu Gln Ile Leu Phe Glu Phe Ala Lys
1130                1135                1140

Glu Met Met Arg Val Val Asp Phe Asn Asn Asn Met Leu Trp
1145                1150                1155

Phe Asn Phe Lys Leu Arg Val Gly Phe Asn His Gly Pro Leu Thr
1160                1165                1170

Ala Gly Val Ile Gly Thr Thr Lys Leu Leu Tyr Asp Ile Trp Gly
1175                1180                1185

Asp Thr Val Asn Ile Ala Ser Arg Met Asp Thr Thr Gly Val Glu
1190                1195                1200

Cys Arg Ile Gln Val Ser Glu Glu Ser Tyr Arg Val Leu Ser Lys
1205                1210                1215

Met Gly Tyr Asp Phe Asp Tyr Arg Gly Thr Val Asn Val Lys Gly
1220                1225                1230

Lys Gly Gln Met Lys Thr Tyr Leu Tyr Pro Lys Cys Thr Asp His
1235                1240                1245

Arg Val Ile Pro Gln His Gln Leu Ser Ile Ser Pro Asp Ile Arg
1250                1255                1260

Val Gln Val Asp Gly Ser Ile Gly Arg Ser Pro Thr Asp Glu Ile
1265                1270                1275

Ala Asn Leu Val Pro Ser Val Gln Tyr Val Asp Lys Thr Ser Leu
1280                1285                1290

Gly Ser Asp Ser Ser Thr Gln Ala Lys Asp Ala His Leu Ser Pro
1295                1300                1305

Lys Arg Pro Trp Lys Glu Pro Val Lys Ala Glu Arg Gly Arg
1310                1315                1320

Phe Gly Lys Ala Ile Glu Lys Asp Asp Cys Asp Glu Thr Gly Ile
1325                1330                1335

Glu Glu Ala Asn Glu Leu Thr Lys Leu Asn Val Ser Lys Ser Val
1340                1345                1350

<210> SEQ ID NO 2
<211> LENGTH: 4062
<212> TYPE: DNA
<213> ORGANISM: human

<400> SEQUENCE: 2

| atggcttccc | cgccccacca | gcagctgctg | catcaccaca | gcaccgaggt | gagctgcgac | 60 |
| --- | --- | --- | --- | --- | --- | --- |
| tccagcgggg | acagcaatgg | cttccccgcc | ccaccagcag | ctgctgcatc | accacagcac | 120 |
| cgaggtgagc | tgcgactcca | gcggggacag | cactctagct | gcagcagctc | tggggactcc | 180 |
| ggggcgtcc | cccggcgagt | gggcggcgga | ggccggctgc | gcaggcagaa | gaagctgccc | 240 |
| cagctgttcg | agagggcctc | cagccgctgg | tgggacccca | gttcgactc | ggtgaacctg | 300 |
| gaggaggcct | gcctggagcg | ctgcttcccg | cagacccagc | gccggttccg | gtatgcgctc | 360 |
| ttctacatcg | gcttcgcctg | ccttctgtgg | agcatctatt | ttgcggtcca | catgagatcc | 420 |
| agactgatcg | tcatggtcgc | cccgcgctg | tgcttcctcc | tggtgtgtgt | gggcttcttt | 480 |
| ctgtttacct | tcaccaagct | gtacgcccgg | cattacgcgt | ggacctcgct | ggctctcacc | 540 |
| ctgctggtgt | tcgccctgac | cctggctgcg | cagttccagg | tcttgacgcc | tgtctcagga | 600 |

-continued

| | |
|---|---|
| cgcggcgaca gctccaacct tacggccaca gcccggccca cagatacttg cttatctcaa | 660 |
| gtggggagct tctccatgtg catcgaagtg ctcttttgc tctataccgt catgcactta | 720 |
| cctttgtacc tgagtttgtg tctggggtg gcctactctg tccttttcga gacctttggc | 780 |
| taccatttcc gggatgaagc ctgcttcccc tcgcccggag ccggggccct gcactgggag | 840 |
| ctgctgagca gggggctgct ccacggctgc atccacgcca tcgggtcca cctgttcgtc | 900 |
| atgtcccagg tgaggtccag gagcaccttc ctcaaggtgg ggcaatccat tatgcacggg | 960 |
| aaggacctgg aagtggaaaa agccctcaaa gagaggatga ttcattccgt gatgccaaga | 1020 |
| atcatagccg atgacttaat gaagcaggga gatgaggaga gtgagaattc tgtcaagagg | 1080 |
| catgccacct cgagcccaa gaacaggaag aaaaagtctt ccatccaaaa agctcctata | 1140 |
| gccttccgcc cttttaagat gcagcagatc gaagaagtca gtatcttatt tgcagatatc | 1200 |
| gtgggcttca ccaagatgag tgccaacaag tctgcccacg ccctggtggg tctcctgaac | 1260 |
| gatctgttcg gtcgcttcga ccgcctgtgt gaggagacca agtgtgagaa aatcagcacc | 1320 |
| ctgggagact gttactactg cgtggcgggc tgtcccgagc ccgggccga ccatgcctac | 1380 |
| tgctgcatcg agatgggcct gggcatgatc aaggccatcg agcagttctg ccaggagaag | 1440 |
| aaggagatgg tgaacatgag agtcggggtg cacacgggca ccgtccttg cggcatcctg | 1500 |
| ggcatgagga ggtttaaatt tgacgtgtgg tccaacgatg tgaacctggc caatctcatg | 1560 |
| gagcagctgg gagtggccgg caaagttcac atttctgagg ccaccgcaaa atacttagat | 1620 |
| gaccggtacg aaatggaaga tgggaaagtt attgaacggc tgggccagag cgtggttgct | 1680 |
| gaccagttga aaggtttgaa gacatacctg atatcgggtc agagagccaa ggagtctcgc | 1740 |
| tgcagctgtg cagaggcctt gctttctggc tttgaggtca ttgacggctc acaggtgtcc | 1800 |
| tcaggcccta ggggacaggg gacagcgtca tcagggaatg tcagtgactt ggcgcagact | 1860 |
| gtcaaaacct ttgataacct taagacctgc ccttcgtgcg gaatcacatt tgctcccaaa | 1920 |
| tctgaagccg gcgccgaggg aggagcacct caaaacggct gccaagacga gcataaaaac | 1980 |
| agcaccaagg cttctggagg acctaatccc aaaactcaga acgggctcct cagccctccc | 2040 |
| caagaggaga agctcaccaa cagtcagact tctctgtgtg agatcttgca ggagaaggga | 2100 |
| aggtgggcag gggtgagcct ggaccagtcg gctctccttc cgctgaggtt caagaacatc | 2160 |
| cgggagaaaa cggacgccca ctttgtggac gttatcaaag aagacagcct gatgaaagat | 2220 |
| tacttttta agccgcccat taatcagttc agcctgaact tcctggatca ggagctggag | 2280 |
| cgatcctaca ggaccagcta tcaggaagag gtcatgaaga actccccgt gaagacgttt | 2340 |
| gctagtccca ccttcagctc cctcctggat gtgtttctgt cgaccacagt gtttctgacg | 2400 |
| ctgtccacca cctgcttcct gaagtacgag gcggccaccg tgcctccccc gcccgccgcc | 2460 |
| ctggcggtct tcagtgcagc cctgctgctg gaggtgctgt ccctcgcggt gtccatcagg | 2520 |
| atggtgttct tcctggagga cgtcatggcc tgcaccaagc gcctgctgga gtggatcgcc | 2580 |
| ggctggctac cacgtcactg catcggggcc atcctggtgt cgcttcccgc actggccgtc | 2640 |
| tactcccatg tcacctccga atatgagacc aacatacact tcccagtgtt cacaggctcg | 2700 |
| gccgcgctga ttgccgtcgt gcactactgt aacttctgcc agctcagctc ctggatgagg | 2760 |
| tcctccctcg ccaccgtcgt gggggccggg ccgctgctcc tgctctacgt ctccctgtgc | 2820 |
| ccagacagtt ctgtattaac ttcgcccctt gacgcagtac agaatttcag ttccgagagg | 2880 |
| aacccgtgca ataggtcggt gccgcgtgac ctccggcggc ccgccagcct catcggccag | 2940 |
| gaggtggttc tcgtcttctt tctcctgctc ttgttggtct ggttcctgaa tcgcgaattt | 3000 |

```
gaagtcagct accgcctcca ctaccacgga gacgtggaag cggatcttca ccgcaccaag    3060
atccagagca tgcgggacca ggcagactgg ctgctgagga acatcatccc ctaccacgtg    3120
gctgagcagc tgaaggtgtc ccagacctac tccaagaacc atgacagcgg aggggtgatc    3180
ttcgccagca tcgtcaactt cagcgagttc tacgaggaga actacgaggg cggcaaggag    3240
tgctaccggg tcctcaacga gctcatcggg gactttgacg agctcctaag caagccggac    3300
tacagcagca tcgagaagat caagaccatc ggagccacgt acatggcggc gtcagggctg    3360
aacaccgcgc aggcccagga cggcagccac ccgcaggagc acctgcagat cctgttcgag    3420
ttcgccaagg agatgatgcg cgtggtggac gacttcaaca acaacatgct gtggttcaac    3480
ttcaagctcc gcgtcggctt caaccatggg cccctcacgg ccggggtcat cggcaccacc    3540
aagctgctgt acgacatctg gggagacacc gtcaacatcg ccagcaggat ggacaccacc    3600
ggcgtggagt gccgcatcca ggtgagcgaa gagagctacc gcgtcttgag caagatgggc    3660
tatgacttcg actacagagg gaccgtgaat gtcaagggga aaggccagat gaagacctac    3720
ctgtacccaa agtgcacgga tcacagggtc atcccacagc accagctgtc catctcccca    3780
gacatccgcg tccaggtgga tggcagcatc ggacggtctc ccacagacga gattgccaac    3840
ctggtgcctt ctgtccagta tgtggacaag acatctctgg gttctgacag cagcacgcag    3900
gccaaggatg cccacctgtc ccccaagaga ccgtggaagg agcccgtcaa agccgaagaa    3960
aggggtcgat ttggcaaagc catagagaaa gacgactgtg acgaaacagg aatagaagaa    4020
gccaacgaac tcaccaagct caacgtttca aagagtgtgt ga                      4062

<210> SEQ ID NO 3
<211> LENGTH: 15
<212> TYPE: DNA
<213> ORGANISM: artificial
<220> FEATURE:
<223> OTHER INFORMATION: Probe

<400> SEQUENCE: 3
aggtcaggaa gaact                                                     15

<210> SEQ ID NO 4
<211> LENGTH: 15
<212> TYPE: DNA
<213> ORGANISM: artificial
<220> FEATURE:
<223> OTHER INFORMATION: Probe

<400> SEQUENCE: 4
aggtcagaaa gaact                                                     15
```